United States Patent
San et al.

(10) Patent No.: US 7,790,416 B2
(45) Date of Patent: *Sep. 7, 2010

(54) **MUTANT *E. COLI* STRAIN WITH INCREASED SUCCINIC ACID PRODUCTION**

(75) Inventors: Ka-Yiu San, Houston, TX (US); George N. Bennett, Houston, TX (US); Ailen Sanchez, South San Francisco, CA (US)

(73) Assignee: Rice University, Houston, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/697,295

(22) Filed: Apr. 5, 2007

(65) Prior Publication Data

US 2007/0184539 A1    Aug. 9, 2007

Related U.S. Application Data

(62) Division of application No. 11/214,309, filed on Aug. 29, 2005, now Pat. No. 7,223,567.

(60) Provisional application No. 60/604,922, filed on Aug. 27, 2004.

(51) Int. Cl.
    C12P 1/00      (2006.01)
    C12P 21/04     (2006.01)
    C12N 1/20      (2006.01)
    C12N 5/00      (2006.01)

(52) U.S. Cl. .............. 435/71.2; 435/41; 435/252.8; 435/325

(58) Field of Classification Search ............. 435/71.2, 435/41, 45, 71.1, 252.3, 325, 383
See application file for complete search history.

(56) References Cited

U.S. PATENT DOCUMENTS

| | | | |
|---|---|---|---|
| 5,770,435 | A | 6/1998 | Donnelly et al. |
| 5,869,301 | A | 2/1999 | Nghiem et al. |
| 6,159,738 | A | 12/2000 | Donnelly et al. |
| RE37,393 | E | 9/2001 | Donnelly et al. |
| 6,448,061 | B1 | 9/2002 | Pan et al. |
| 6,455,284 | B1 | 9/2002 | Gokarn et al. |
| 6,743,610 | B2 | 6/2004 | Donnelly et al. |
| 7,262,046 | B2 | 8/2007 | Ka-Yiu et al. |
| 7,569,380 | B2 * | 8/2009 | San et al. ............... 435/252.3 |
| 2003/0087381 | A1 | 5/2003 | Gokarn et al. |
| 2005/0042736 | A1 | 2/2005 | San et al. |
| 2006/0073577 | A1 | 4/2006 | Ka-Yiu et al. |
| 2006/0128001 | A1 | 6/2006 | Yukawa et al. |
| 2006/0141594 | A1 | 6/2006 | San et al. |

FOREIGN PATENT DOCUMENTS

WO    WO 2007/001982    1/2007

OTHER PUBLICATIONS

Hong et al., 2001, Metabolic flux analysis for succinic acid production by recombinant *Escherichia coli* with amplified malic enzyme activity Biotechhnol. Bioeng 74:89-95.*
Mijts et al 2003, Engineering of secondary metabolite pathways. Curr Opin Biotechnol. Dec. 2003;14(6):597-602.*
Bunch et al., Mutants of *Escherichia coli* deficient in the fermentative lactate dehydrogenase Microbiology. Jan. 1997;143 ( Pt 1):187-95.*
Mat-Jan et al., Mutants of *Escherichia coli* deficient in the fermentative lactate dehydrogenase. J Bacteriol. Jan. 1989;171(1):342-8.*
Yang et al., The effects of feed and intracellular pyruvate levels on the redistribution of metabolic fluxes in *Escherichia coli* Metabolic Engineering vol. 3, Issue 2, Apr. 2001, pp. 115-123.*
Sánchez et al., Novel pathway engineering design of the anaerobic central metabolic pathway in *Escherichia coli* to increase succinate yield and productivity Metabolic Engineering vol. 7, Issue 3, May 2005, pp. 229-239.*
Wendisch VF et al., Metabolic engineering of *Escherichia coli* and Corynebacterium glutamicum for biotechnological production of organic acids and amino acids Curr Opin Microbiol. Jun. 2006;9(3):268-74. Epub Apr. 17, 2006.*
Alam, K et al., Anaerobic fermentation balance of *E. coli* as observed by in vivo nuclear magnetic resonance spectroscopy; J. of Bacteriology, vol. 171(11), pp. 6213-6217, Nov. 1989.
Amann, et al., Gene 69:301-15 (1988).
Aristidou AA, San KY, Bennett GN. Metabolic engineering of *Escherichia coli* to enhance recombinant protein production through acetate reduction. Biotechnol Prog. Jul.-Aug. 1995;11(4):475-8.
Aristidou AA, San KY, Bennett GN. Metabolic flux analysis of *Escherichia coli* expressing the *Bacillus subtilis* acetolactate synthase in batch and continuous cultures. Biotechnol Bioeng. Jun. 20, 1999;63(6):737-49.

(Continued)

*Primary Examiner*—Maria Leavitt
(74) *Attorney, Agent, or Firm*—Baker & McKenzie LLP

(57) ABSTRACT

The invention relates to a mutant strain of bacteria, which either lacks or contains mutant genes for several key metabolic enzymes, and which produces high amounts of succinic acid under anaerobic conditions.

6 Claims, 5 Drawing Sheets

OTHER PUBLICATIONS

Berrios-Rivera SJ, Bennett GN, San KY. Metabolic engineering of *Escherichia coli*: increase of NADH availability by overexpressing an NAD(+)-dependent formate dehydrogenase. Metab Eng. Jul. 2002;4(3):217-29.

Bunch, et al. Microbiology 143:187-195 (1997).

Chatterjee, et al. Appl Environ Microbiol. 67:148-54 (2001).

Cox, et al. Development of a metabolic network design and optimization framework incorportating implementation constraints: a succinate production case study. Metab. Eng. Submitted (2005).

Clark, et al. "Mutants of *Escherichia coli* defective in acid fermentation," Appl. Biochem. Biotechnol. 17:163-73 (Apr. 1988).

Datsenko and Wanner. Proc Natl Acad Sci U S A. 97:6640-5 (2000).

Dittrich, C. R.; Vadali, R. V.; Bennett, G. N.; San, K.-Y. Redistribution of metabolic fluxes in the central aerobic metabolic pathway of *E.coli* mutant strains with deletion of the ackA-pta and poxB pathways for the production of isoamyl acetate. 2005.

Donnelly,et al. App. Biochem. Biotech. 70-72:187-98 (1998).

Duckworth and Tong. Biochemistry 15:108-114 (1976).

Gokarn, et al., App. Microbiol. Biotechnol. 56:188-95 (2001).

Gokarn, R. R.; Eiteman, M. A.; Altman, E. Expression of pyruvate carboxylase enhances succinate production in *Escherichia coli* without affecting glucose uptake rate. Biotech. Let. 1998, 20, 795-798.

Gokarn, R. R.; Eiteman, M. A.; Altman, E. Metabolic analysis of *Escherichia coli* in the presence and absense of the carboxylating enzymes phosphoenolpyruvate carboxylase and pyruvate carboxylase. Appl Environ Microbiol. (2000) 666, 1844-1850.

Goldberg, et al., App. Environ. Microbiol. 45:1838-47 (1983).

Guyer, et al. Cold Spring Harbor Symp. Quant. Biol. 45:135-40 (1981).

Hahm, D. H.; Pan, J. G.; Rhee, J. S. Characterization and evaluation of a pta (phosphotransacetylase) negative mutant of *Escherichia coli* HZB101 as a production host of foreign lipase. Appl Microbiol Biotechnol. 1994, 42, 100-107.

Hespell, et al., "Stabilization of pet operon plasmids and ethanol production in *Escherichia coli* strains lacking lactate dehydrogenase and pyruvate formate-lyase activities," Appl Environ Microbiol. 62:4594-7 (Dec. 1996).

Holms, W. H. The central metabolic pathways in *Escherichia coli*: relationship between flux and control at a branchpoint, efficiency of conversion to biomass, and excretion of acetate. Curr Top Cell Regul. 1986, 28, 69-105.

Hong, S. H.; Lee, S.-Y. Importance of redox balance on the production of succinic acid by metabolically engineered *Escherichia coli*. Appl Microbiol Biotechnol. 2002, 58, 286-290.

Lee, S.J., et al., Metabolic engineering of *Escherichia coli* for enhanced production of succinic acid, based on genome comparison and insilico gene knockout simulation. Appl Environ Microbiol. 71:7880-7 (2005).

Leonardo, M. et al., Anaerobic regulation of the adhE gene, encoding the fermentative alcohol dehydrogenase of *E. coli*; J. of Bacteriology, vol. 175(3), pp. 870-878, Feb. 1993.

Levanon SS, San KY, Bennett GN. Effect of oxygen on the *Escherichia coli* ArcA and FNR regulation systems and metabolic responses.Biotechnol Bioeng. Mar. 5, 2005;89(5):556-64.

Lin H, Bennett GN, San KY. Genetic reconstruction of the aerobic central metabolism in *Escherichia coli* for the absolute aerobic production of succinate. Biotechnol Bioeng. Jan. 20, 2005;89(2):148-56.

Lin H, San KY, Bennett GN. Effect of *Sorghum vulgare* phosphoenolpyruvate carboxylase and *Lactococcus lactis* pyruvate carboxylase coexpression on succinate production in mutant strains of *Escherichia coli*.Appl Microbiol Biotechnol. Nov. 24, 2004; pp. 1-16.

Lin H, Vadali RV, Bennett GN, San KY. Increasing the acetyl-CoA pool in the presence of overexpressed phosphoenolpyruvate carboxylase or pyruvate carboxylase enhances succinate production in *Escherichia coli*. Biotechnol Prog. Sep.-Oct. 2004;20(5):1599-604.

Lin H. et al. Metabolic engineering of aerobic succinate production systems in *Escherichia coli* to improve process productivity and achieve the maximum theoretical succinate yield. Metab Eng. Mar. 2005;7(2):116-27.

Lin, et al. Biotechnol. Bioeng. 90:775-9 (2005).

Lin, et al. J. Ind. Microbiol. Biotechnol. 32:87-93 (2005).

Lin, H. "Metabolic Network Design and Engineering in *E. coli*" Ph.D. Thesis, Rice University, Dept. of Bioengineering (2005).

Luli, G. W.; Strohl, W. R. Comparison of growth, acetate production, and acetate inhibition of *Escherichia coli* strains in batch and fed-batch fermentations. Applied and Environmental Microbiology. 1990, 56, 1004-1011.

Mat-Jan, et al. J. Bact. 171:342-8 (1989).

Maurus, et al. Biochemistry 42:5555-65 (2003).

Millard, et al.,. App. Environ. Microbiol. 62:1808-10 (1996).

Park, D. et al., Utilization of electrically reduced neutral red by *Actinobacillus succinogenes*: physiological functio of neutral red in membrane-driven fumarate reduction and energy conservation; J. of Bacteriology, vol. 181(8), pp. 2403-2410, Apr. 1999.

Phillips, G. J.; Park, S. K.; Huber, D. High copy number plasmids compatible with commonly used cloning vectors. Biotechniques. 2000, 28, 400-408.

Sanchez, A. M.; Bennett, G. N.; San, K.-Y. Novel pathway engineering design of the anaerobic central metabolic pathway in *Escherichia coli* to increase succinate yield and productivity. Metab. Eng. 7:229-39 (2005b).

Sanchez, et al. Biotechnol. Prog. 21:358-65 (2005a).

Sanchez, et al., J. Biotechnol. 117:395-405 (2005c).

Stockell et al. J. Biol. Chem. 278:35435-43 (2003).

Stols and Donnelly App. Environ. Microbiol. 63:2695-701 (1997).

Stryer, Biochemistry, Third edition, 1975, W. H. Freeman and Company, New York, pp. 374-375.

Tolentino et al., Biotech. Let. 14:157-62. (1992).

Underwood, et al., App. Environ. Microbiol. 68:1071-81 (2002).

Varadarajan and Miller, Biotechnol. Prog. 15:845-854 (1999).

Vemuri, et al. J. Ind. Microbiol. Biotechnol. 28:325-32 (2002).

Vemuri, G. N.; Eiteman, M. A.; Altman, E. Effect of growth mode and pyruvate carboxylase on succinic acid production by metabolically engineered strains of *Escherichia coli*. Appl Environ Microbiol. 2002, 68, 1715-1727.

Volkert, et al., J. Bact. 176:1297-302 (1994).

Wang, et al. App. Biochem. Biotechnol. 70-72:919-28 (1998).

Wang, et al., App. Environ. Microbiol. 66:1223-7 (2000).

Wang, et al., J. Biol. Chem. 267:16759-62. (1992).

Yang et al., Metab. Eng. 1, 141-152 (1999b).

Yang YT, Aristidou AA, San KY, Bennett GN. Metabolic flux analysis of *Escherichia coli* deficient in the acetate production pathway and expressing the *Bacillus subtilis* acetolactate synthase. Metab Eng. Jan. 1999;1(1):26-34.

Yang YT, Bennett GN, San KY. Effect of inactivation of nuo and ackA-pta on redistribution of metabolic fluxes in *Escherichia coli*. Biotechnol Bioeng. Nov. 5, 1999;65(3):291-7.

Yang YT, Bennett GN, San KY. The effects of feed and intracellular pyruvate levels on the redistribution of metabolic fluxes in *Escherichia coli*. Metab Eng. Apr. 2001;3(2):115-23.

Yang YT, Peredelchuk M, Bennett GN, San KY. Effect of variation of *Klebsiella pneumoniae* acetolactate synthase expression on metabolic flux redistribution in *Escherichia coli*. Biotechnol Bioeng. Jul. 20, 2000;69(2):150-9.

Yanisch-Perron, et al., Gene 33:103-19 (1985).

Zeikus, et al., App. Microbiol. Biotechnol. 51:545-52 (1999).

Brown, T.D.K., et al., The enzymic interconversion of acetate and acetyl-coenzyme A in *Escherichia coli*. Journal of General Microbiology 102:327-336 (1977).

\* cited by examiner

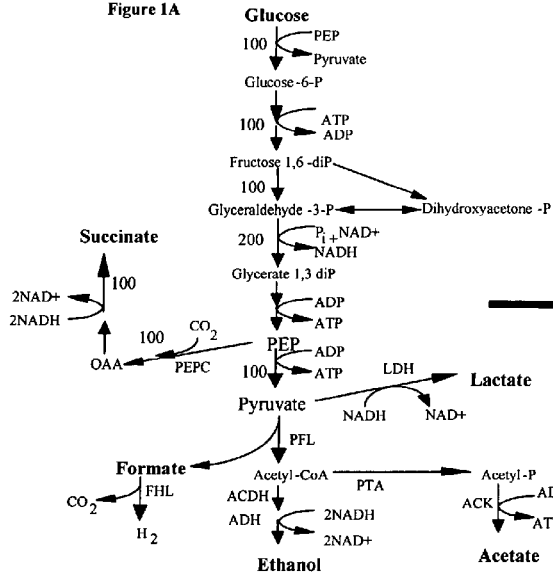
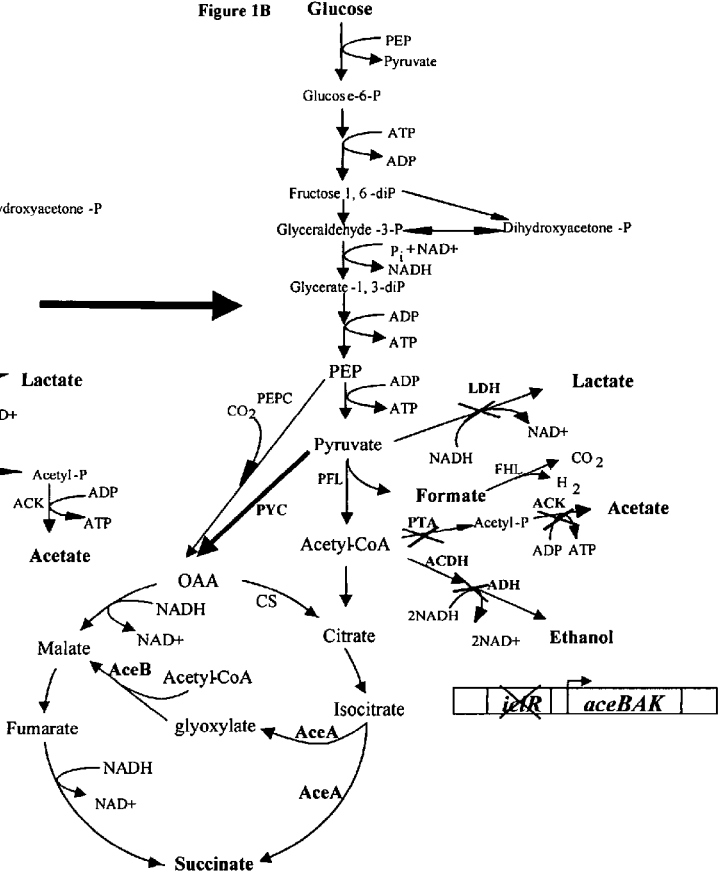
Figure 1A
Figure 1B

MUTANT E. COLI STRAIN WITH INCREASED SUCCINIC ACID PRODUCTION

PRIOR RELATED APPLICATIONS

This application is a divisional application of U.S. Ser. No. 11/214,309, filed Aug. 29, 2005, now U.S. Pat. No. 7,223,567, which claims the benefit of U.S. Provisional Application Ser. No. 60/604,922 filed Aug. 27, 2004, entitled "Mutant E. coli Strain with Increased Succinic Acid Production," which is incorporated herein in its entirety.

FEDERALLY SPONSORED RESEARCH STATEMENT

The present invention was developed with funds from the National Science Foundation. Therefore, the United States Government may have certain rights in the invention.

REFERENCE TO MICROFICHE APPENDIX

Not applicable.

REFERENCE TO A SEQUENCE LISTING

Not applicable.

FIELD OF THE INVENTION

The invention relates to methods of producing succinic acid, malic acid, fumaric acid, and other carboxylic acids in metabolically engineered microorganisms.

BACKGROUND OF THE INVENTION

The valuable specialty chemical succinate and its derivatives have extensive industrial applications. Succinic acid is used as a raw material for food, medicine, plastics, cosmetics, and textiles, as well as in plating and waste-gas scrubbing (61). Succinic acid can serve as a feedstock for such plastic precursors as 1,4-butanediol (BDO), tetrahydrofuran, and gamma-butyrolactone. Further, succinic acid and BDO can be used as monomers for polyesters. If the cost of succinate can be reduced, it will become more useful as an intermediary feedstock for producing other bulk chemicals (47). Along with succinic acid, other 4-carbon dicarboxylic acids such as malic acid and fumaric acid also have feedstock potential.

The production of succinate, malate, and fumarate from glucose, xylose, sorbitol, and other "green" renewable feedstocks (in this case through fermentation processes) is an avenue to supplant the more energy intensive methods of deriving such acids from nonrenewable sources. Succinate is an intermediate for anaerobic fermentations by propionate-producing bacteria but those processes result in low yields and concentrations. It has long been known that mixtures of acids are produced from E. coli fermentation. However, for each mole of glucose fermented, only 1.2 moles of formic acid, 0.1-0.2 moles of lactic acid, and 0.3-0.4 moles of succinic acid are produced. As such, efforts to produce carboxylic acids fermentatively have resulted in relatively large amounts of growth substrates, such as glucose, not being converted to desired product.

Numerous attempts have been made to metabolically engineer the anaerobic central metabolic pathway of E. coli to increase succinate yield and productivity (7, 8, 12, 14, 15, 20, 24, 32, 44, 48). Genetic engineering coupled with optimization of production conditions have also been shown to increase succinate production. An example is the growth of a succinate producing mutant E. coli strain using dual phase fermentation production mode which comprises an initial aerobic growth phase followed by an anaerobic production phase or/and by changing the headspace conditions of the anaerobic fermentation using carbon dioxide, hydrogen or a mixture of both gases (35, 49).

Specifically, manipulating enzyme levels through the amplification, addition, or reduction of a particular pathway can result in high yields of a desired product. Various genetic improvements for succinic acid production under anaerobic conditions have been described that utilize the mixed-acid fermentation pathways of E. coli. One example is the overexpression of phosphoenolpyruvate carboxylase (pepc) from E. coli (34). In another example, the conversion of fumarate to succinate was improved by overexpressing native fumarate reductase (frd) in E. coil (17, 53). Certain enzymes are not indigenous in E. coli, but can potentially help increase succinate production. By introducing pyruvate carboxylase (pyc) from Rhizobium etli into E. coli, succinate production was enhanced (14, 15, 16). Other metabolic engineering strategies include inactivating competing pathways of succinate. When malic enzyme was overexpressed in a host with inactivated pyruvate formate lyase (pfl) and lactate dehydrogenase (ldh) genes, succinate became the major fermentation product (44, 20). An inactive glucose phosphotransferase system (ptsG) in the same mutant strain (pfl- and idh-) had also been shown to yield higher succinate production in E. coli and improve growth (8).

The maximum theoretical yield (molar basis) of succinate from glucose under anaerobic conditions is limited to 1 mol/mol, assuming that all the carbon flux will go through the native succinate fermentative pathway (FIG. 1). The fermentative pathway converts oxaloacetate (OAA) to malate, fumarate and then succinate and this pathway requires 2 moles of NADH per mole of succinate produced. One major obstacle to high succinate yield through the fermentative pathway is due to NADH limitation. This is because one mole of glucose can provide only two moles of NADH through the glycolytic pathway; however, the formation of one mole of succinate through the native fermentative pathway requires two moles of NADH. Anaerobic production of succinate is also hampered by the limitations of slow cell growth and production.

Metabolic engineering has the potential to considerably improve process productivity by manipulating the throughput of metabolic pathways. Specifically, manipulating enzyme levels through the amplification, addition, or deletion of a particular pathway can result in high yields of a desired product. What is needed in the art is an improved bacterial strain that produces higher levels of succinate and other carboxylic acids than heretofore provided.

SUMMARY OF THE INVENTION

Bacteria with more than two pathway proteins inactivated to improve carboxylic acid production under anaerobic conditions are described wherein the carboxylic acid produced is succinate, fumarate, malate, oxaloacetate, or glyoxylate. In one embodiment of the invention, the proteins ADHE, LDHA, ACKA, PTA, ICLR, and ARCA are inactivated. In another embodiment of the invention various combinations of proteins are inactivated including ADHE, LDHA, ACKA, PTA, ICLR, and ARCA. Inactivation of these proteins can also be combined with the overexpression of ACEA, ACEB, ACEK, PEPC, PYC, or CITZ to further increase succinate yield.

In one embodiment of the invention, disruption strains are created wherein the adhE, ldhA, iclR, arcA, and ack-pta genes are disrupted. In another embodiment of the invention various combinations of the adhE, ldhA, iclR, arcA, and ack-pta genes are disrupted. The mutant strains designated SBS330MG, SBS440MG, SBS550MG, SBS660MG, and SBS990MG, provide some embodiments of the invention.

Further, an anaerobic method of producing carboxylic acids with a mutant bacterial strain is described, wherein said method comprises inoculating a culture with a mutant bacterial strain described above, culturing said bacterial strain under anaerobic conditions, and isolating carboxylic acids from the media. Bacteria strains can be cultured in a flask, a bioreactor, a fed batch bioreactor, or a chemostat bioreactor to obtain carboxylic acids. Carboxylic acid yield can be further increased by culturing the cells under aerobic conditions before succinate production under anaerobic conditions.

Additionally, modifying the glycolytic flux in bacteria to distribute carboxylic acid through the OAA-citrate and OAA-malate pathway is demonstrated. The glycolytic flux can be a ratio between 10-40% citrate and between 90-60% malate, more preferably about 30% citrate and about 70% malate. The bacterial strains described above partition glycolytic flux in this manner.

BRIEF DESCRIPTION OF THE DRAWINGS

The accompanying drawings which are incorporated in and constitute a part of this specification exemplify the invention and together with the description, serve to explain the principles of the invention.

FIG. 1 Genetically Engineered Anaerobic Metabolic Pathways. NADH competing pathways: lactate (LDH), ethanol (ADH), and acetate pathway (ACK-PTA). The opening of the glyoxylate bypass (ICLR knockout) and the overexpression of a heterologous pyruvate carboxylase (PYC) from L. lactis. The genetically engineered strain depicted here represents strain SBS550MG.

DESCRIPTION OF EMBODIMENTS OF THE INVENTION

Figure 2:
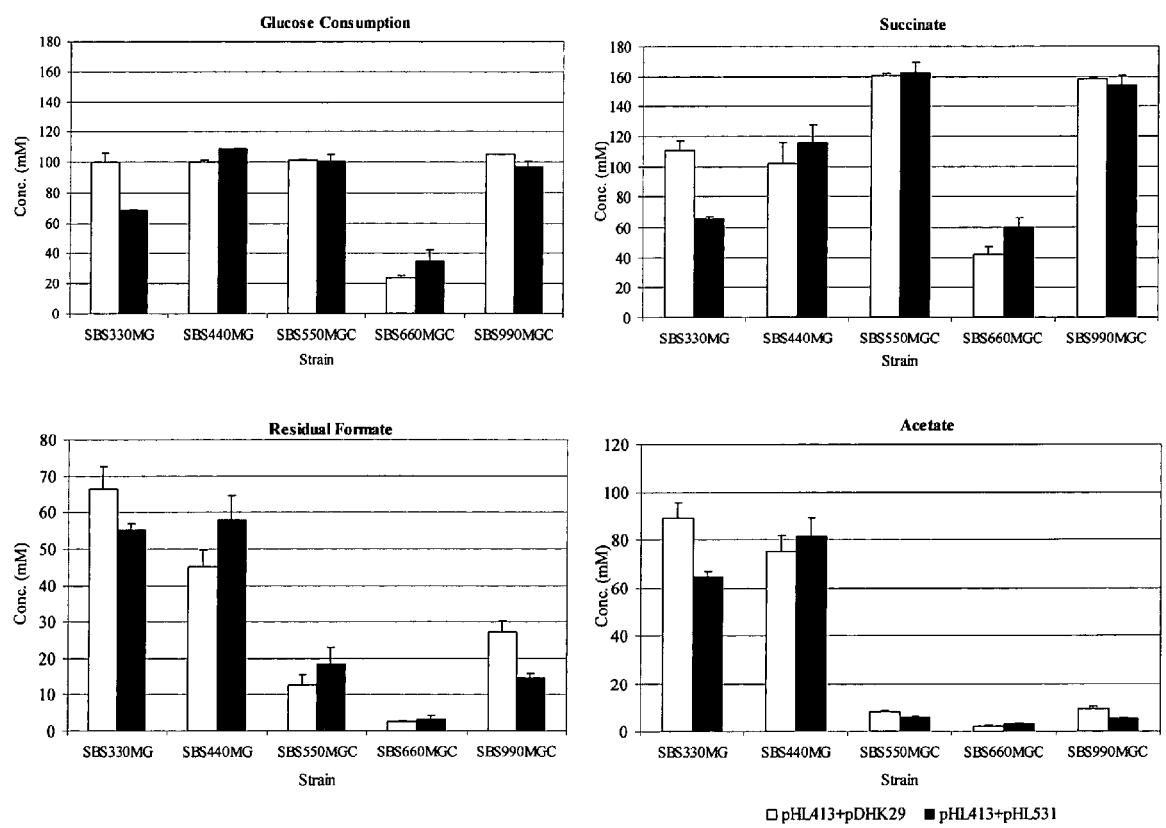
FIG. 2 Glucose Consumption and Production Concentration of Various Strains.

Carboxylic acids described herein can be a salt, acid, base, or derivative depending on structure, pH, and ions present. For example, the terms "succinate" and "succinic acid" are used interchangeably herein. Succinic acid is also called butanedioic acid ($C_4H_6O_4$). Chemicals used herein include formate, glyoxylate, lactate, malate, oxaloacetate (OAA), phosphoenolpyruvate (PEP), and pyruvate. Bacterial metabolic pathways including the Krebs cycle (also called citric acid, tricarboxylic acid, or TCA cycle) can be found in Principles of Biochemistry, by Lehninger as well as other biochemistry texts.

The terms "operably associated" or "operably linked," as used herein, refer to functionally coupled nucleic acid sequences.

"Reduced activity" or "inactivation" is defined herein to be at least a 75% reduction in protein activity, as compared with an appropriate control species. Preferably, at least 80, 85, 90, 95% reduction in activity is attained, and in the most preferred embodiment, the activity is eliminated (100%). Proteins can be inactivated with inhibitors, by mutation, or by suppression of expression or translation, and the like.

"Overexpression" or "overexpressed" is defined herein to be at least 150% of protein activity as compared with an appropriate control species. Overexpression can be achieved by mutating the protein to produce a more active form or a form that is resistant to inhibition, by removing inhibitors, or adding activators, and the like. Overexpression can also be achieved by removing repressors, adding multiple copies of the gene to the cell, or upregulating the endogenous gene, and the like.

The terms "disruption" and "disruption strains," as used herein, refer to cell strains in which the native gene or promoter is mutated, deleted, interrupted, or down regulated in such a way as to decrease the activity of the gene. A gene can be completely (100%) reduced by knockout or removal of the entire genomic DNA sequence. Use of a frame shift mutation, early stop codon, point mutations of critical residues, or deletions or insertions, and the like, can completely inactivate (100%) gene product by completely preventing transcription and/or translation of active protein.

As used herein "recombinant" is relating to, derived from, or containing genetically engineered material.

Genes are abbreviated as follows: isocitrate lyase (aceA a.k.a. icl); malate synthase (aceB); thy glyoxylate shunt operon (aceBAK); isocitrate dehydrogenase kinase/phosphorylase (aceK); acetate kinase-phosphotransacetylase (acKA-pta); alcohol dehydrogenase (adhE); aerobic respiratory control regulator A and B (arcAB); peroxide sensitivity (arg-lac); alcohol acetyltransferases 1 and 2 (atf1 and atf2); putative cadaverine/lysine antiporter (cadR); citrate synthase (citZ); fatty acid degradation regulon (fadR); fumarate reductase (frd); fructose regulon (fruR); fumarase A, B, or C (fumABC); isocitrate dehydrogenase (icd); isocitrate lyase (icl); aceBAK operon repressor (iclR); lactate dehydrogenase (ldhA); malate dehydrogenase (mdh); phosphoenol pyruvate carboxylase (pepC); pyruvate formate lyase (pfl); pyruvate oxidase (poxB); phosphotransferase system genes F and G (ptsF and ptsG); pyruvate carboxylase (pyc); guanosine 3',5'-bispyrophosphate synthetase I (relA1); ribosomal protein S12 (rpsL); and succinate dehydrogenase (sdh). Δlac(arg-lac) 205(U169) is a chromosomal deletion of the arg-lac region that carries a gene or genes that sensitizes cells to $H_2O_2$ (51). PYC can be derived from various species, Lactococcus lactis pyc is expressed as one example (AF068759).

Abbreviations: ampicillin (Ap); oxacillin (Ox); carbenicillin (Cn); chloramphenicol (Cm); kanamycin (Km); streptomycin (Sm); tetracycline (Tc); nalidixic acid (Nal); erythromycin (Em); ampicillin resistance ($Ap^R$); thiamphenicol/chloramphenicol resistance ($Thi^R/Cm^R$); macrolide, lincosamide and streptogramin A resistance ($MLS^R$); streptomycin resistance ($Sm^R$); kanamycin resistance ($Km^R$); Gram-negative origin of replication (ColE1); and Gram-positive origin of replication (OriII). Common restriction enzymes and restriction sites can be found at NEB® (NEW ENGLAND BIOLABS®, www.neb.com) and INVITROGEN® (www.invitrogen.com). ATCC®, AMERICAN TYPE CULTURE COLLECTION™ (www.atcc.org).

Plasmids and strains used in certain embodiments of the invention are set forth in Tables 1 and 2. MG1655 is a $F^-\lambda^-$ spontaneous mutant deficient in F conjugation and as reported by Guyer, et al. (18). Pathway deletions were performed using P1 phage transduction and the one-step inactivation based on λ red recombinase (10). The construction of plasmids and mutant *E. coli* strains were performed using standard biochemistry techniques referenced herein and described in Sambrook (38) and Ausebel (5).

TABLE 1

PLASMIDS

| Plasmid | Genotype | Ref |
|---|---|---|
| pTrc99A | Cloning vector $Ap^R$ | 1 |
| pDHC29 | Cloning vector $Cm^R$ | 37 |
| pDHK29 | Cloning vector $Km^R$ | 37 |
| pUC19 | Cloning vector $Ap^R$ | 60 |
| pHL413 | *L. lactis* pyc in pTrc99A, $Ap^R$ | 40 |
| pCPYC1 | *L. lactis* pyc $Cm^R$ | 54 |
| pHL531 | NADH insensitive citZ in pDHK29, $Km^R$ | 41 |
| pLOI2514 | *B. subtilis* citZ in pCR2.1-TOPO $Km^R/Ap^R$ | 46 |

TABLE 2

STRAINS

| Strain | Genotype | Ref | ATCC # |
|---|---|---|---|
| GJT001 | MC4100(ATC35695) cadR mutant Δlac(arg-lac) U169rpsL150relA1ptsFSm$^R$ | 45 | |
| MG1655 | Wild type (F⁻λ⁻) | 18 | 47076™ |
| MG1655 arcA | ΔarcA::Km$^R$ | 23 | |
| CD55K | ΔldhA::Km$^R$ | 11 | |
| YBS121 | Δack-pta::Cm$^R$ | 56 | |
| HL5K | ΔiclR::Km$^R$ | 28 | |
| SBS100MG | ΔadhE, Km$^R$ | 41 | |
| SBS110MG | ΔadhEΔldhA, Km$^S$ | 40 | |
| SBS330MG | ΔadhEΔldhAΔiclR, Km$^S$ | 41 | |
| SBS440MG | ΔadhEΔldhAΔiclRΔarcA, Km$^S$ | 41 | |
| SBS990MGC | ΔadhEΔldhAΔack-pta::Cm$^R$ | 41 | |
| SBS550MG | ΔadhEΔldhAΔiclRΔack-pta::Cm$^R$ | 41 | |
| SBS660MGC | ΔadhEΔldhAΔiclRΔarcA-Δack-pta::Cm$^R$ | 41 | |

For each experiment the strains were freshly transformed with plasmid if appropriate. A single colony was restreaked on a plate containing the appropriate antibiotics. A single colony was transferred into a 250 ml shake flask containing 50 ml of LB medium with appropriate antibiotics and grown aerobically at 37° C. with shaking at 250 rpm for 12 hours. Cells were washed twice with LB medium and inoculated at 1% v/v into 2 L shake flasks containing 400 ml each of LB medium with appropriate antibiotic concentration and grown aerobically at 37° C. with shaking at 250 rpm for 12 hours. Appropriate cell biomass (~1.4 gCDW) was harvested by centrifugation and the supernatant discarded. The cells were resuspended in 60 ml of anaerobic LB medium (LB broth medium supplemented with 20 g/L of glucose, 1 g/L of NaHCO3) and inoculated immediately into the reactor to a concentration of approximately 10 $OD_{600}$.

Fermentations were conducted under fully anaerobic conditions. A 1 L bioreactor with an initial volume of LB medium of 0.66 L with appropriate antibiotics. At time zero, the reactor was inoculated to an OD600 of approximately 10 as described. The initial concentrations of glucose, antibiotics and cell density in the reactor described are the concentrations after accounting for the dilution by the inoculum when the inoculum is sufficient to change culture concentrations. The pH was maintained at 7.0 with 1.0 M $Na_2CO_3$ and a constant flow rate of 0.2 L/min $CO_2$ was sparged through the culture during the fermentation period. The temperature and agitation were maintained at 37° C. and 250 rpm respectively.

The samples for determination of glucose and product concentrations were withdrawn from the reactor and filtered through a 0.2 μm filter and immediately analyzed by HPLC.

Example 1

Removal of NADH Competing Pathways

Alcohol dehydrogenase (adhE) and lactate dehydrogenase (ldhA) activity was reduced in SBS110MG to address the loss of NADH to the production of alcohol and lactate at the expense of succinate (39). SBS110MG (pTrc99A) consumed 11% of the initial glucose with low succinate yield and high acetate yields.

Example 2

Expression of Pyruvate Carboxylase

Expression of the heterologous PYC from *Lactococcus lactis* (plasmid pHL413) helps to increase the OAA pool by the direct conversion of pyruvate into OAA, which serves as a precursor of the glyoxylate and fermentative pathway, both of which lead to succinic acid production as depicted in FIG. 1. Strain SBS990MG showed lower ICL and MS activities than SBS330MG (pHL413) and SBS550MG (pHL413) as expected due to an active iclR, however, the basal enzyme levels seem to be sufficient to drive the glyoxylate pathway.

The heterologous expression of PYC in succinate producing *E. coli* strains increases the flux from pyruvate to OAA. PYC diverts pyruvate toward OAA to favor succinate generation. SBS110MG harboring plasmid pHL413, which encodes the heterologous pyruvate carboxylase from *L. lactis*, produced 15.6 g/L (132 mM) of succinate from 18.7 g/L (104 mM) of glucose after 24 h of culture in an atmosphere of $CO_2$ yielding 1.3 mol of succinate per mole of glucose. The effectiveness of increasing OAA to increase succinate production was demonstrated.

Example 3

Activating the Glyoxylate Shunt

The inactivation of ICLR diverts acetyl CoA towards the production of succinic acid by activation of the aceBAK operon thus decreasing the carbon flux through acetate and continuing the recycling of acetyl CoA. In strain SBS330MG (pHL413) ACK-PTA is active and therefore little flow of carbon is diverted to the glyoxylate even when this pathway had been genetically activated. The activity of the glyoxylate pathway is evidenced by the higher enzyme activity showed by this strain with respect to the wild type control (data not shown). The strains with higher ICL and MS activities were SBS330MG (pHL413) and SBS550MG (pHL413). These strains showed more than twice the activity of the wild type strain. Strain SBS330MG was created as an intermediate strain by inactivating the iclR gene in adh, ldh mutant, SBS110MG. In an ldhA adhE mutant acetyl-CoA is diverted towards the glyoxylate pathway therefore reducing acetate excretion. Even when the glyoxylate pathway has been constitutively activated in this strain, acetyl-CoA is channeled through the acetate pathway.

Figure 3:
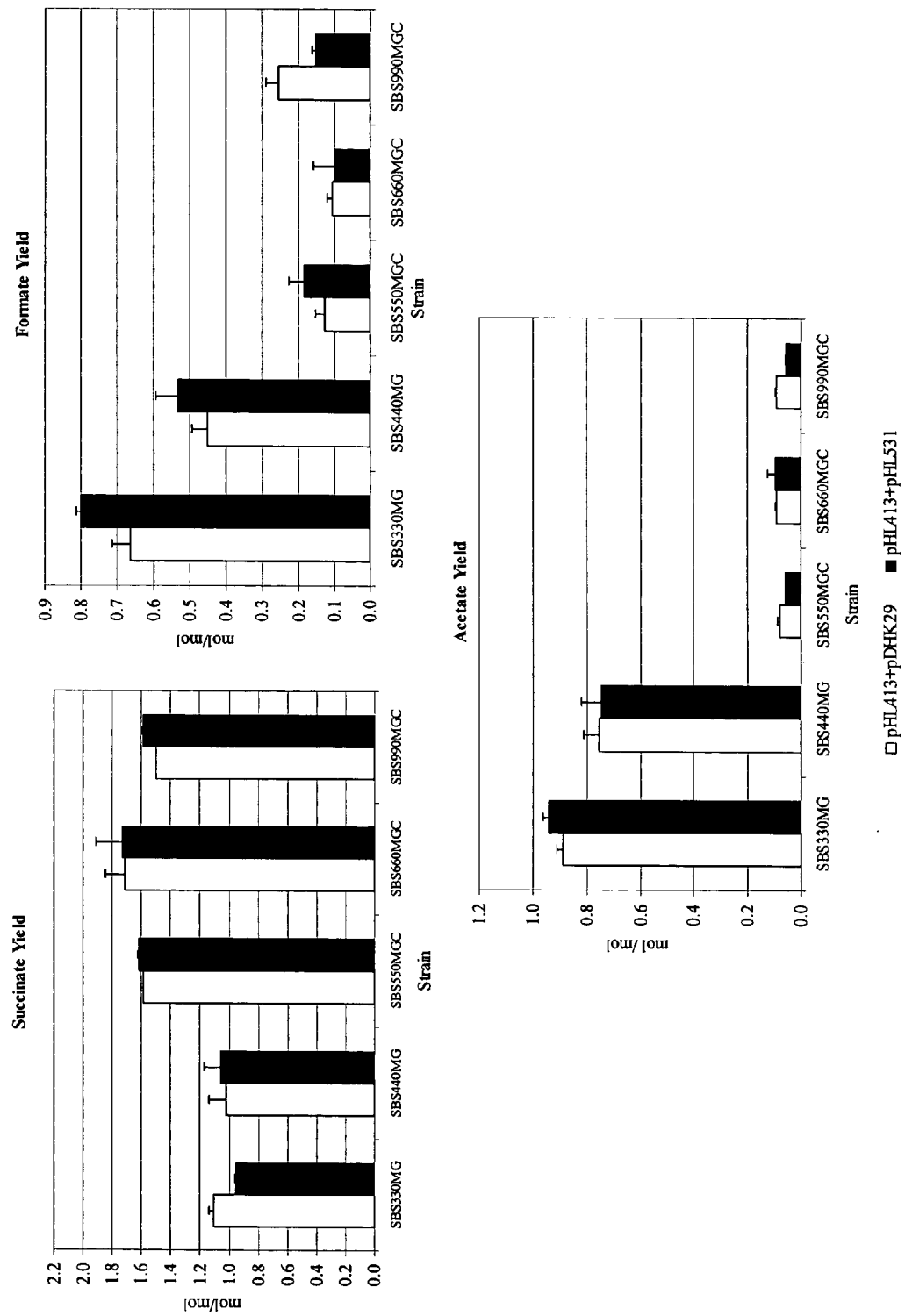
FIG. 3 Product Yield in Various Strains.
Figure 4:
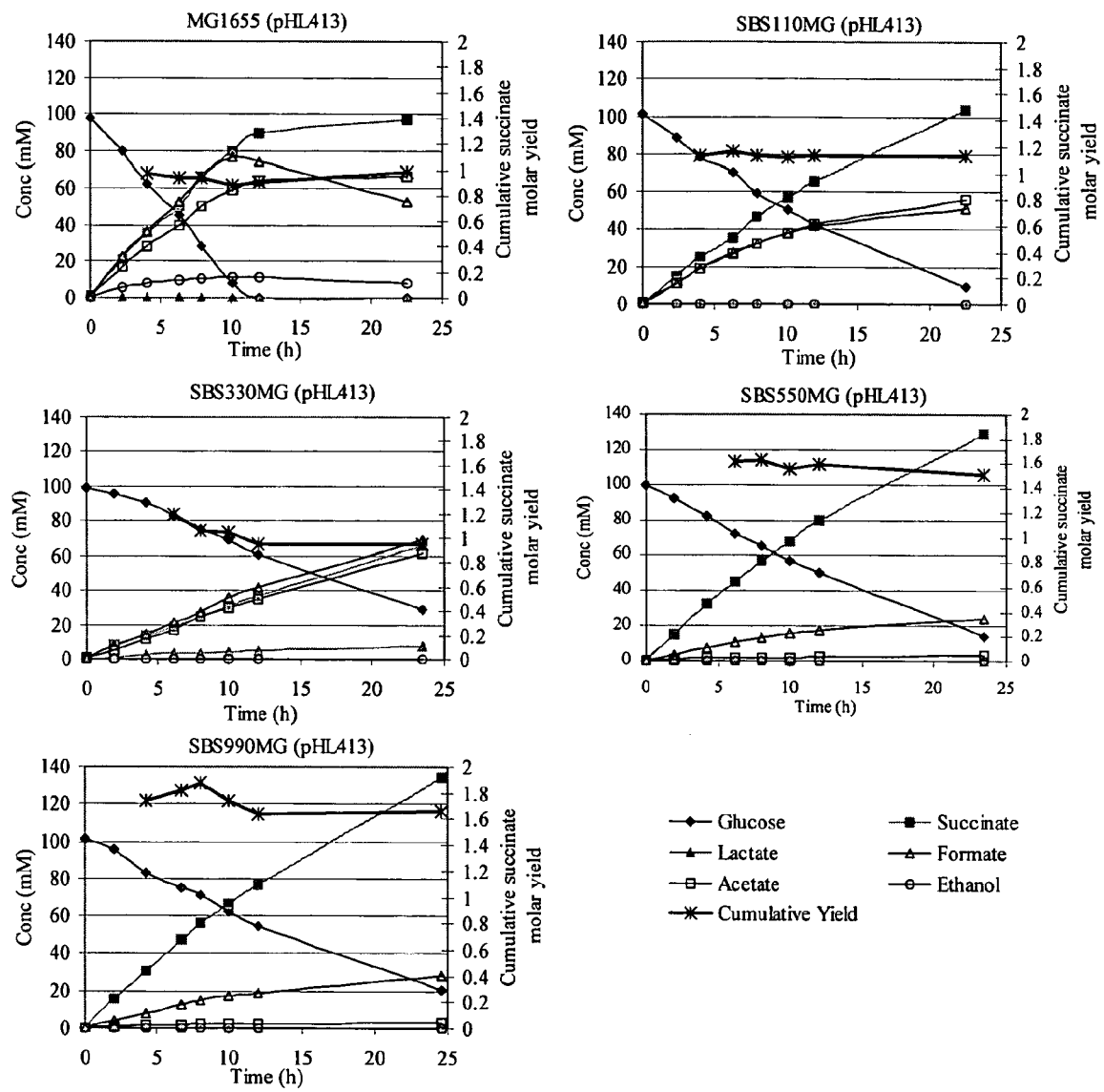
FIG. 4 Cumulative Succinate Yield in Mutant Strains.

As seen in FIG. 3, the SBS330MG strain produced 1.1 mol/mol succinate per glucose, 0.66 mol/mol formate per glucose, and 0.89 mol/mol acetate per glucose. Although SBS330MG(pHL413) produced significant succinate, it also produced the highest levels of formate and acetate.

Example 4

Removal of Aerobic Respiratory Control

The ARCA protein belongs to the two-component (ARCB-ARCA) signal-transduction systems family, and in concert with its cognate sensory kinase ARCB, represents a global regulation system that negatively or positively controls the expression of many operons such as several dehydrogenases of the flavoprotein class, terminal oxidases, tricarboxylic acid cycle, enzymes of the glyoxylate shunt and enzymes of the pathway for fatty acid degradation. Mutant strain SBS440MGC contains a mutant version of arcA, a gene encoding a protein involved in the control of aerobic respiration.

The deletion of arcA in the SBS440MGC strain produced 1.02 mol/mol succinate per glucose, 0.45 mol/mol formate per glucose, and 0.75 mol/mol acetate per glucose, as seen in FIG. 3. The removal of ARCA did not dramatically affect glucose consumption (FIG. 2), but decreased overall succinate yield slightly (FIG. 3).

Example 5

Reducing Acetate Production

In strain SBS990MGC, acetate kinase-phosphotransacetylase (ackA-pta) was reduced in an alcohol dehydrogenase (adhE) and lactate dehydrogenase (ldhA) background to increase succinate production and reduce NADH consumption through ethanol and lactate production. Deletion of the ack and pta genes eliminates the major acetate formation pathway. Although mutant strain SBS990MG contains adhE, ldhA and ack-pta deletions, SBS990MG still has an intact iclR. Active ICLR may reduce ACEBAK expression, but residual ACEA and ACEB enzyme activity may still allow residual glyoxylate shunt activity.

Increased NADH availability in SBS990MG has been implemented to increase succinate yield from glucose to 1.6 mol/mol under fully anaerobic conditions (FIGS. 2 and 3). SBS990MG was able to achieve a high succinate yield.

Example 6

Dual Succinate Synthesis Route

A pathway design with an activate glyoxylate pathway was previously developed and examined in silico (9) and implemented in vivo by genetically engineering *E. coli* (41) to increase succinate yield and alleviate the NADH availability constraint. Strain SBS550MG (pHL413) was constructed to posses a dual succinate synthesis route which diverts required quantities of NADH through the traditional fermentative pathway and maximizes the carbon converted to succinate by balancing the carbon flux through the fermentative pathway and the glyoxylate pathway (which has lower NADH requirement) (41). The redesigned pathway showed an experimental NADH requirement from glucose of ~1.25 moles of NADH per mole of succinate in contrast to the theoretical requirement of 2 moles of NADH per mole of succinate in the wild type *E. coli* strain.

Inactivation of ack-pta in an ldhA adhE iclR mutant proved to be the key to channel acetyl-CoA towards the glyoxylate pathway. The deletion of the acetate pathway helped conserve carbon molecules in the form of acetyl-CoA which is diverted to the formation of glyoxylate and succinate. Further conversion of glyoxylate to malate to fumarate and finally to succinate also helped reduce the NADH requirement. This pathway only requires one mole of NADH to produce two moles of succinate from 2 moles of acetyl-CoA and 1 mole of OAA (41).

The performance of strain SBS550MG overexpressing PYC was examined and the results are shown in FIG. 2. Although strain SBS550MG with PYC can grow reasonably well under anaerobic conditions, aerobic conditions were used in this study to accumulate biomass faster before subjecting the cells to the anaerobic succinate production phase. Strain SBS550MG with and without pHL531 consumed 100% of the glucose, and both strains produced similar levels of succinic acid (160 mM) from 100 mM glucose. An increase in residual formate and decrease in acetate levels was observed with the strain carrying the plasmid pHL531 which overexpresses the NADH insensitive citrate synthase. The acetate levels found in cultures of SBS550MG-based strains were much lower than the acetate levels found in cultures of SBS110MG (pHL413). Succinate yields of SBS550MG (pHL413, pHL531) and SBS550MG (pHL413, pDHK29) were very similar (about 1.6 mol/mol succinate per glucose).

The fact that the high succinic acid yield of 1.6 mol/mol remains unchanged despite the overexpression of the NADH insensitive citrate synthase also suggested that the native citrate synthase system is already sufficient to drive the glyoxylate pathway. In addition, the results further showed that the dual-route succinate production system is very robust; the system was able to handle significant perturbations at the OAA node without significant changes in yield. Apparently the cells are capable of achieving a balanced partition between the fermentative and the glyoxylate pathway in terms of available reducing equivalents and carbon atoms to efficiently maximal succinic acid production.

Cultures of the SBS660MG-based strains consumed only 25-35% of the glucose at the end of 24 hours. Both SBS660MG(pHL413, pHL531) and SBS660MG(pHL413, pDHK29) strains produced similar succinate yields of approximately 1.7 mol/mol. These yield values are among the highest of all the strains studied (Table 3). No significant difference was observed in the succinic acid, acetate or formate yield of the transformed mutant strain SBS660MG (pHL413, pHL531) relative to its control (FIG. 3). Deletion of arcA increased succinate production per mol glucose, but reduced glucose consumption.

Example 7

Expression of Citrate Synthase

FIG. 1 depicts the various metabolites produced in the *E. coli* mutant strains, SBS550MG, SBS660MGC and SBS990MGC transformed with the pyruvate carboxylase encoding plasmid pHL413 and the citrate synthase expression plasmid pHL531. The acetate yield in SBS330MG (pHL413) increased with respect to the control and SBS110MG (pHL413). These results suggest that there could be some inhibition of citrate synthase caused by the higher NADH levels and favored by lower NAD+ levels. It is well known that NADH inhibits citrate synthase allosterically (33, 43) and NAD+ is a weak competitive inhibitor of NADH binding (13). The absolute in vitro CITRATE SYNTHASE activity observed in SBS330MG (pHL413) was the lowest of all the strains studied.

Strain SBS550MG (pHL413+pDHK29) was used as the control, and SBS550MG (pHL413+pHL531) co-expresses heterologous PYC and citrate synthase. Strain SBS550MG with and without pHL531 consumed 100% of the glucose, and both strains produced similar levels of succinic acid (160 mM) from 100 mM glucose. Despite the fact that the acetate pathway was knocked out, low concentrations of acetate were detected in the cultures at the end of the fermentation. An increase in residual formate and decrease in acetate levels was observed with the strain carrying the plasmid pHL531 which overexpresses the NADH insensitive citrate synthase.

TABLE 3

CARBOXYLIC ACID YIELD[A]

| Strain | Succinic acid | Formate | Acetate |
|---|---|---|---|
| SBS550MG (pHL413 + pDHK29) | 1.59 ± 0.01 | 0.13 ± 0.03 | 0.08 ± 0.01 |
| SBS550MG (pHL413 + pHL531) | 1.61 ± 0.01 | 0.18 ± 0.04 | 0.06 ± 0.00 |
| SBS660MG (pHL413 + pDHK29) | 1.72 ± 0.13 | 0.11 ± 0.01 | 0.09 ± 0.00 |
| SBS660MG (pHL413 + pHL531) | 1.73 ± 0.18 | 0.10 ± 0.06 | 0.10 ± 0.03 |
| SBS990MG (pHL413 + pDHK29) | 1.50 ± 0.00 | 0.26 ± 0.03 | 0.09 ± 0.01 |
| SBS990MG (pHL413 + pHL531) | 1.58 ± 0.01 | 0.15 ± 0.01 | 0.06 ± 0.00 |

[A]mol of product/mol of glucose during a 24 hr anaerobic production phase

The expression of the NADH citrate synthase in the SBS660MG(pHL413, pHL531) strain increased the glucose consumption as well as the metabolites produced by about 40% when compared with the SBS660MG(pHL413, pDH29) control strain. Both SBS660MG(pHL413, pHL531) and SBS660MG(pHL413, pDHK29) strains produced similar succinate yields of approximately 1.7 mol/mol. These yield values are among the highest of all the strains studied (Table 3). The succinic acid level produced by the SBS990MG (pHL413, pDHK29) strain was very similar to that of the SBS550MG(pHL413, pDHK29) strain.

The results showed that the dual-route succinate production system is very robust; the system was able to handle significant perturbations at the OAA node without significant changes in yield. The engineered cells are capable of achieving a balanced partition between the fermentative and the glyoxylate pathway in terms of available reducing equivalents and carbon atoms to efficiently maximal succinic acid production. These results further support the hypothesis that there might be some degree of activation of the glyoxylate pathway when adhE, ldhA and ack-pta are inactivated.

Example 8

NADH Flux Analysis

Measured fluxes obtained under batch cultivation conditions were used to estimate intracellular fluxes and identify critical branch point flux split ratios. The comparison of changes in branch point flux split ratios to the glyoxylate pathway and the fermentative pathway at the OAA node as a result of different mutations revealed the sensitivity of succinate yield to these manipulations.

A metabolic matrix was constructed based on the law of mass conservation and on the pseudo-steady state hypothesis (PSSH) on the intracellular intermediate metabolites. The stoichiometric matrix obtained from the set of linear equations formulated based on the metabolic network shown in FIG. 1 gave a square matrix of dimensions 15×15 based on solely the measured metabolites, PSSH balances on the intracellular metabolites and NADH balance. For the NADH balance it was assumed that the NADH production and consumption must be equal. Derivation of the redox balance does not take into account any carbon assimilated into biomass. The biomass ($v_2$) was assumed to be zero for all the mutants except the wild type and was used as a measurement which produced an overdetermined system where the solution was found by least-squares fit. The mathematical representation, stoichiometric matrix and net conversion equations relating the various species in the network are presented in Table 4: Enzymatic Reactions.

TABLE 4

ENZYMATIC REACTIONS

| Reaction | Enzyme(s) |
|---|---|
| 1 Glucose + PEP ↔Glucose 6-P + Pyruvate | Glucose: PTS enzymes; Enzyme I, HPr, $II^{Glc}$, $III^{Glc}$ |
| 2 Glucose-6-P ↔Biomass | |
| 3 Glucose 6-P + ATP ↔2 Glyceraldehyde 3-P + ADP | |
| a. Glucose 6-P ↔Fructose 6-P | Glucose-6-phosphate isomerase |
| b. Fructose-6-P + ATP ↔Fructose 1,6-diP + ADP | Phosphofructokinase, PFK |
| c. Fructose 1,6-diP ↔Dihydroxyacetone-P + Glyceraldehyde 3-P | Fructose-diP aldolase |
| d. Dihydroxyacetone-P ↔Glyceraldehyde 3-P | Triose-P isomerase |
| 4 Glyceraldehyde 3-P + $NAD^+$ + $P_i$ + 2ADP ↔Pyruvate + $H_2O$ + NADH + $H^+$ + 2ATP | |
| a. Glyceraldehyde 3-P + $NAD^+$ + $P_i$ ↔Glycerate 1,3-diP + NADH + $H^+$ | 3-P Glyceraldehyde dehydrogenase |
| b. Glycerate 1,3-diP + ADP ↔Glycerate 3-P + ATP | 3-P glycerate kinase |
| c. Glycerate 3-P ↔Glycerate 2-P | P glycerate mutase |
| d. Glycerate 2-P ↔PEP + $H_2O$ | Enolase |
| e. PEP + ADP ↔Pyruvate + ATP | Pyruvate kinase |
| 5 I. PEP + $CO_2$ ↔OAA + $P_i$ | PEP carboxylase |
| II. Pyr + ATP + $CO_2$ ↔oxaloacetate + ADP + $P_i$ | Pyruvate carboxylase |
| 6 Pyruvate + NADH ↔lactate + $NAD^+$ | Lactate dehydrogenase |
| 7 Pyruvate + HSCoA ↔Formate + Acetyl-CoA | Pyruvate formate-lyase |
| 8 Formate ↔$CO_2$ + $H_2$ | Formate hydrogen lyase |
| 9 Acetyl-CoA + $P_i$ + ADP ↔Acetate + HSCoA + ATP | |
| a. Acetyl-CoA + $P_i$ ↔Acetyl-P + HSCoA | Acetate phosphotransferase, PTA |
| b. Acetyl-P + ADP ↔Acetate + ATP | Acetate kinase, ACK; or, chemical hydrolysis |
| 10 Acetyl-CoA + 2 NADH + 2 $H^+$ ↔Ethanol + HSCoA + 2 $NAD^+$ | |
| a. Acetyl-CoA + NADH + $H^+$ ↔Acetaldehyde + HSCoA + $NAD^+$ | Aldehyde dehydrogenase |
| b. Acetaldehyde + NADH + $H^+$ ↔Ethanol + $NAD^+$ | Alcohol dehydrogenase |
| 11 2 acetyl-CoA + $H_2O$ + oxaloacetate ↔Malate + Succinate HSCoA + CoA | |
| a. acetyl-CoA + $H_2O$ + oxaloacetate ↔citrate + CoA | Citrate synthase |
| b. citrate ↔isocitrate | Aconitate hydratase |
| c. Isocitrate ↔glyoxalate + succinate | Isocitrate lyase |
| d. glyoxalate + acetylCoA ↔Malate + HSCoA | Malate synthase |
| 12 oxaloactetate + NADH ↔Fumarate + $NAD^+$ + $H_2O$ | |
| a. oxaloactetate + NADH ↔Malate + $NAD^+$ | Malate dehydrogenase |
| b. malate ↔fumarate + $H_2O$ | Fumarase C |
| 13 Fumarate + NADH + $P_i$ + ADP ↔Succinate + $NAD^+$ + ATP | Fumarate reductase |

Vector r(t) (m×1), where m=15, 16 or 17) denotes the net conversion rates for the various metabolites:

$$r^T = [r_1 \ldots r_8\ 000000000]$$

For MG1655 (pHL413), the balances for H2 and biomass were excluded, therefore matrix A was reduced to a 15×15 square matrix. The exact solution was obtained by equation 1:

$$\upsilon(t) = A^{-1} r(t) \quad (1)$$

For the mutant strains SBS110MG (pHL413), SBS330MG (pHL413), SBS550MG (pHL413) and SBS990MG (pHL413) exclusion of the H2 balance and inclusion of biomass gave as a result an overdetermined system (m=16 and n=15) which was solved using the least squares fit approach and was estimated according to the following equation 2:

$$\upsilon(t) = (A^T A)^{-1} A^T r(t) \quad (2)$$

The glycolytic fluxes ($\upsilon_1$ through $\upsilon_4$) of strain SBS550MG (pHL413) increased with respect to SBS330MG (pHL413) but decreased with respect to the wild type control strain. The PFL flux ($\upsilon_7$) also decreased with respect to the wild type control strain causing a major reduction in the acetate and formate flux. These glycolytic fluxes demonstrate that high succinate yield is dependent upon partitioning of carboxylic acid production between OAA-citrate and OAA-malate. The flux partitioning balances NADH consumption and leads to increased production of succinate. Partitioning in high succinate producing strains varies between 10-40% citrate derived succinate and 90-60% malate derived succinate production (see FIG. 1).

TABLE 5

METABOLIC FLUXES

| Flux | To: | MG1655 (pHL413) | SBS110MG (pHL413) | SBS330MG (pHL413) | SBS550MG (pHL413) | SBS990MG (pHL413) |
|---|---|---|---|---|---|---|
| v1 | Glucose Uptake* | 3.46 | 2.78 | 1.28 | 2.13 | 1.96 |
| v2 | Biomass | 0.07 | 0.00 | 0.00 | 0.00 | 0.00 |
| v3 | G-3-P | 3.38 | 2.83 | 1.37 | 2.16 | 2.08 |
| v4 | PEP + Pyruvate | 6.77 | 5.66 | 2.77 | 4.32 | 4.19 |
| v5 | OAA | 2.90 | 2.94 | 1.31 | 2.57 | 2.53 |
| v6 | Lactate* | 0.00 | 0.00 | 0.21 | 0.00 | 0.00 |
| v7 | Intracellular Formate | 3.87 | 2.74 | 1.27 | 1.76 | 1.72 |
| v8 | $H_2$ | 0.42 | 0.27 | 0.00 | 0.77 | 0.63 |
| v9 | Acetate* | 2.58 | 2.35 | 1.22 | 0.14 | 0.12 |
| v10 | Ethanol* | 0.65 | 0.00 | 0.00 | 0.00 | 0.00 |
| v11 | Glyoxylate Succinate | 0.32 | 0.21 | 0.05 | 0.82 | 0.83 |
| v12 | Malate | 2.58 | 2.74 | 1.28 | 1.76 | 1.72 |
| v13 | Intracellular Succinate | 2.90 | 2.97 | 1.35 | 2.58 | 2.58 |
| $v_{RF}$ | Residual Formate* | 3.45 | 2.47 | 1.62 | 0.99 | 1.09 |
| $v_{ES}$ | Excreted Succinate* | 3.22 | 3.19 | 1.43 | 3.41 | 3.44 |
| | $CO_2$ | -2.48 | -2.67 | -1.31 | -1.80 | -1.90 |
| | Succinate Yield | 0.93 | 1.15 | 1.12 | 1.60 | 1.75 |
| | $(NADH)_U$/Gl | 1.96 | 2.04 | 2.17 | 2.03 | 2.14 |
| | $(NADH)_s$/Succinate | 1.70 | 1.79 | 1.83 | 1.27 | 1.25 |

The estimation of the time varying concentrations of excreted metabolites was determined between t=0 h and t=6 h or 7 h and based on the average cell density as follows (4):

$$r_i = \frac{C_i(t + \delta t) - C_i(t)}{\delta t \times \overline{X}} \quad (3)$$

$$\text{Where, } \overline{X} = \frac{X(t + \delta t) - X(t)}{\ln\left\{\frac{X(t + \delta t)}{X(t)}\right\}} \quad (4)$$

It was found that the succinate yield is relatively more sensitive to the split ratio at the OAA node than at the PEP/PYR node. The most favorable split ratio to obtain the highest succinate yield was the fraction partition of OAA to glyoxylate of 0.32 and 0.68 to the fermentative pathway obtained in strains SBS550MG (pHL413) and SBS990MG (pHL413). The succinate yields achieved in these two strains were 1.6 mol/mol and 1.7 mol/mol respectively. It has been shown that an active glyoxylate pathway in an ldhA, adhE, ack-pta mutant strain is responsible for the high succinate yields achieved anaerobically. High intracellular levels of NADH and acetyl-CoA compared to the wild type were found in SBS550MG (pHL413) and SBS990MG (pHL413) at the onset of the anaerobic fermentation, but these levels rapidly dropped suggesting that these strains are capable of handling high glycolytic fluxes in spite of inactivation of enzymes downstream of the PEP/PYR branch point.

Example 9

Fed Batch Anaerobic Fermentation

Figure 5:
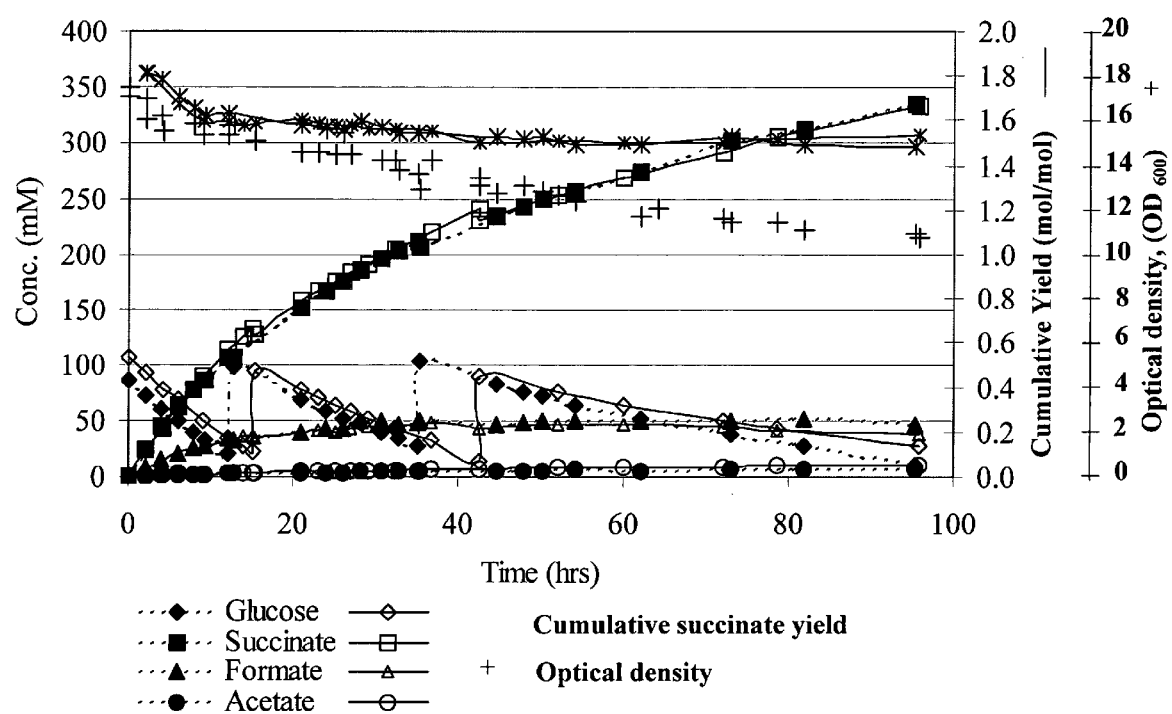
FIG. 5 Fed Batch Production with strain SBS550MG (pHL413). Solid symbols correspond to the metabolites measured on a first run and open symbols correspond to the metabolites measured on a replicate run. Glucose was added in pulses when glucose dropped to about 20 mM as indicated by the arrows.

A bioreactor generates higher productivity due to a more controlled environment. A batch experiment was performed in duplicate to examine the efficiency of SBS550(pHL314) in producing succinate under controlled conditions (FIG. 5). In this experiment, the bioreactor was initially charged with LB and supplemented with 86 mM of glucose. At time zero, the reactor was inoculated to an OD of 17. Glucose was added in pulses when glucose dropped to about 20 mM as indicated by the arrows. Differences in initial glucose concentration and in glucose addition time between runs did not affect strain performance.

As seen in FIG. 5, the strain is very efficient in producing succinic acid. The succinic acid production ranges from 12 to 9 mM of succinate/hr with a very efficient yield of 1.6 mole/mole. The system only produced very minute quantities of other metabolites, such as formate and acetate as byproducts. It is also expected that the system can be further optimized to improve succinate yield to 1.8, 1.9, or 2.0 mole/mole, or even higher.

All of the references cited herein are expressly incorporated by reference. References are listed again here for convenience:

1. Alam, et al., J. Bact. 171:6213-7 (1989).
2. Amann, et al., Gene 69:301-15 (1988).
3. Aristodou, et al., Biotechnol. Prog. 11:475-8 (1995).

4. Aristodou, et al. Biotechnol. Bioeng. 63:737-49 (1999).
5. Ausebel, "Current Protocols in Molecular Biology" Greene Pub. Assoc.
6. Berrios-Rivera, et al. Metab. Eng. 4:217-29 (2002).
7. Bunch, et al. Microbiology 143:187-195 (1997).
8. Chatterjee, et al. Appl Environ Microbiol. 67:148-54 (2001).
9. Cox, et al. Development of a metabolic network design and optimization framework incorporating implementation constraints: a succinate production case study. Metab. Eng. Submitted (2005).
10. Datsenko and Wanner. Proc Natl Acad Sci U S A. 97:6640-5 (2000).
11. Dittrich, et al. Biotechnol. Prog. 21:627-31 (2005).
12. Donnelly, et al. App. Biochem. Biotech. 70-72:187-98 (1998).
13. Duckworth and Tong. Biochemistry 15:108-114 (1976).
14. Gokarn, et al., Biotech. Let. 20:795-8 (1998).
15. Gokarn, et al., Appl. Environ. Microbiol. 66:1844-50 (2000).
16. Gokarn, et al., App. Microbiol. Biotechnol. 56:188-95 (2001).
17. Goldberg, et al., App. Environ. Microbiol. 45:1838-47 (1983).
18. Guyer, et al. Cold Spring Harbor Symp. Quant. Biol. 45:135-40 (1981).
19. Hahm, et al., Appl. Microbiol. Biotechnol. 42:100-7 (1994).
20. Hong and Lee, Appl. Microbiol. Biotechnol. 58:286-90 (2002).
21. Lehninger, et al. "Principles of Biochemistry, $2^{nd}$ ed." Worth Pub., New York (1993).
22. Leonard, et al., J. Bact. 175: 870-8 (1993).
23. Levanon, et al. Biotechnol. Bioeng. 89:556-64 (2005).
24. Lin, et al. Biotechnol. Prog. 20:1599-604 (2004).
25. Lin, et al. Biotechnol. Bioeng. 89:148-56 (2005).
26. Lin, H. "Metabolic Network Design and Engineering in *E. coli*" Ph.D. Thesis, Rice University, Dept. of Bioengineering (2005).
27. Lin, et al. J. Ind. Microbiol. Biotechnol. 32:87-93 (2005).
28. Lin, et al. Metab. Eng. 7:116-27 (2005).
29. Lin, et al. Appl. Microbiol. Biotechnol. 67:515-23 (2005).
30. Lin, et al. Biotechnol. Bioeng. 90:775-9 (2005).
31. Luli and Strohl, Appl. Environ. Microbiol. 56:1004-11 (1990).
32. Mat-Jan, et al. J. Bact. 171:342-8 (1989).
33. Maurus, et al. Biochemistry 42:5555-65 (2003).
34. Millard, et al., App. Environ. Microbiol. 62:1808-10 (1996).
35. Nghiem, et al. U.S. Pat. No. 5,869,301 (1999).
36. Park, et al. J. Bact. 181:2403-10 (1999).
37. Phillips, et al., Biotechniques. 28:400-8 (2000).
38. Sambrook, Fritsch, and Maniatis, "Molecular Cloning—A Laboratory Manual, 2nd ed." Cold Spring Harbor Laboratory, New York (1989).
39. San, et al. U.S. Application 20050042736.
40. Sanchez, et al. Biotechnol. Prog. 21:358-65 (2005a).
41. Sanchez, et al., Metab. Eng. 7:229-39 (2005b).
42. Sanchez, et al., J. Biotechnol. 117:395-405 (2005c).
43. Stockell et al. J. Biol. Chem. 278:35435-43 (2003).
44. Stols and Donnelly App. Environ. Microbiol. 63:2695-701 (1997).
45. Tolentino et al., Biotech. Let. 14:157-62. (1992).
46. Underwood, et al., App. Environ. Microbiol. 68:1071-81 (2002).
47. Varadarajan and Miller, Biotechnol. Prog. 15:845-54 (1999).
48. Vemuri, et al., Appl. Environ. Microbiol. 68:1715-27 (2002).
49. Vemuri, et al. J. Ind. Microbiol. Biotechnol. 28:325-32 (2002).
50. Voet and Voet, "Biochemistry $2^{nd}$ ed." John Wiley & Sons, New York (1995).
51. Volkert, et al., J. Bact. 176:1297-302 (1994).
52. Wang, et al., J. Biol. Chem. 267:16759-62. (1992).
53. Wang, et al. App. Biochem. Biotechnol. 70-72:919-28 (1998).
54. Wang, et al., App. Environ. Microbiol. 66:1223-7 (2000).
55. Yang, et al. Biotechnol. Bioeng. 65:291-7 (1999).
56. Yang, et al., Metab. Eng. 1:26-34 (1999).
57. Yang, et al., Metab. Eng. 1:141-52 (1999).
58. Yang, et al., Biotechnol. Bioeng. 69:150-9 (2000).
59. Yang, et al., Metab. Eng. 3:115-23 (2001).
60. Yanisch-Perron, et al., Gene 33:103-19 (1985).
61. Zeikus, et al., App. Microbiol. Biotechnol. 51:545-52 (1999).

What is claimed is:

1. A method of producing succinate comprising:
   a) generating a genetically engineered *Escherichia coli* bacterial cell comprising a disruption of:
      i) lactate dehydrogenase (ldh), ii) alcohol dehydrogenase (adh), iii) aceBAK operon repressor (iclR), and iv) both acetate kinase and phosphotransacetylase (ack-pta),
   b) culturing said bacteria under anaerobic conditions in a bioreactor, wherein a glycolytic flux from oxaloacetate (OAA) is partitioned in a ratio between 10-40% citrate and between 90-60% malate, wherein said bacteria produces greater than 1.5 moles of succinate per mol of glucose.

2. The method of claim 1, wherein said glycolytic flux is partitioned in a ratio of about 30% citrate and about 70% malate.

3. The method of claim 1, wherein said bacteria comprise an expression construct encoding pyruvate carboxylase (pyc), wherein said pyc is from *Lactobacillus lactis*.

4. A method of producing succinic acid comprising:
   a) generating a genetically engineered *Escherichia coli* bacterial cell comprising a disruption of:
      i) ldh, ii) adh, iii) iclR, and iv) ack-pta,
   b) culturing said bacteria under anaerobic conditions in a fed-batch reactor, wherein a glycolytic flux from oxaloacetate (OAA) is partitioned in a ratio between 10-40% citrate and between 90-60% malate, wherein said bacteria produces greater than 1.5 moles of succinic acid per mol of glucose.

5. The method of claim 4, wherein said glycolytic flux is partitioned in a ratio of about 30% citrate and about 70% malate.

6. The method of claim 4, wherein said bacteria comprise an expression construct encoding pyc, wherein said pyc is from *Lactobacillus lactis*.

* * * * *